US009329524B2

(12) United States Patent
Izawa et al.

(10) Patent No.: US 9,329,524 B2
(45) Date of Patent: May 3, 2016

(54) APPARATUS FOR DETECTING A TONER DENSITY OF A LIQUID DEVELOPER

(71) Applicants: Hideo Izawa, Narashino (JP); Kotaro Harada, Narashino (JP); Sumito Mera, Narashino (JP)

(72) Inventors: Hideo Izawa, Narashino (JP); Kotaro Harada, Narashino (JP); Sumito Mera, Narashino (JP)

(73) Assignee: MIYAKOSHI PRINTING MACHINERY CO., LTD., Narashino-shi (JP)

( * ) Notice: Subject to any disclaimer, the term of this patent is extended or adjusted under 35 U.S.C. 154(b) by 386 days.

(21) Appl. No.: 13/862,949

(22) Filed: Apr. 15, 2013

(65) Prior Publication Data
US 2013/0294790 A1    Nov. 7, 2013

(30) Foreign Application Priority Data

Apr. 18, 2012  (JP) .................. 2012-094484

(51) Int. Cl.
*G03G 15/08*    (2006.01)
*G01N 29/024*   (2006.01)
*G03G 15/10*    (2006.01)

(52) U.S. Cl.
CPC .......... *G03G 15/0824* (2013.01); *G01N 29/024* (2013.01); *G03G 15/0849* (2013.01); *G03G 15/105* (2013.01); *G01N 2291/02818* (2013.01)

(58) Field of Classification Search
CPC ............... G01N 29/024; G01N 2291/02818; G03G 15/105; G03G 15/0849; G03G 15/0824; G03G 15/104; G03G 2215/0658; G03G 15/0856; G03G 2215/0888

USPC ........................... 399/57, 237, 58, 53
See application file for complete search history.

(56) References Cited

U.S. PATENT DOCUMENTS

| 4,943,735 | A | 7/1990 | Nishikawa |
| 6,379,796 | B1 * | 4/2002 | Uenishi et al. ............... 428/398 |
| 6,558,450 | B2 * | 5/2003 | Sengupta et al. ............... 95/46 |

(Continued)

FOREIGN PATENT DOCUMENTS

| EP | 1 243 310 A2 | 9/2002 |
| JP | 6-314031 A | 11/1994 |

(Continued)

OTHER PUBLICATIONS

European Search Report dated Jun. 18, 2013, issued in corresponding European Patent Application No. 13164116.9.
Office Action dated Apr. 30, 2015, issued in counterpart Japanese Application No. 2012-094484, (2 pages).

*Primary Examiner* — Hezron E Williams
*Assistant Examiner* — Marrit Eyassu
(74) *Attorney, Agent, or Firm* — Westerman, Hattori, Daniels & Adrian, LLP

(57) ABSTRACT

A deaerator and a density detector are provided in a liquid developer circulating path through which the liquid developer in a main tank is circulated, wherein the deaerator includes a bundle of hollow fibers each forming a hollow fiber membrane whose inside is depressurized and over whose outer peripheral surface the liquid developer is forced to flow under pressure, thereby sufficiently removing dissolved air in the liquid developer, and a toner density of the liquid developer is detected when the liquid developer of which dissolved air is sufficiently removed is passed through the density detector utilizing ultrasonic waves, making it possible to detect the toner density with a high degree of precision.

7 Claims, 3 Drawing Sheets

(56) References Cited

U.S. PATENT DOCUMENTS

| | | |
|---|---|---|
| 6,648,945 B1 | 11/2003 | Takeda et al. |
| 2004/0146317 A1* | 7/2004 | Park .............................. 399/237 |
| 2006/0093404 A1* | 5/2006 | Chou et al. ................... 399/237 |
| 2008/0079759 A1* | 4/2008 | Nagashima .................... 347/10 |
| 2009/0167829 A1 | 7/2009 | Iijima |
| 2009/0175642 A1* | 7/2009 | Izawa et al. .................... 399/57 |
| 2011/0058838 A1 | 3/2011 | Ritzer et al. |

FOREIGN PATENT DOCUMENTS

| | | |
|---|---|---|
| JP | 06-314031 A | 11/1994 |
| JP | 2002-370006 A | 12/2002 |
| JP | 2006-281532 A | 10/2006 |
| JP | 2008-014930 A | 1/2008 |
| JP | 2009-163124 A | 7/2009 |

* cited by examiner

APPARATUS FOR DETECTING A TONER DENSITY OF A LIQUID DEVELOPER

TECHNICAL FIELD

The present invention relates to an apparatus for detecting a toner density of a liquid developer that is used in a wet-type electrophotographic printer.

BACKGROUND ART

In a wet-type electrophotographic printer using a liquid developer, inasmuch as its toner density impacts the printing quality (image density) of a printed matter, it has hitherto been practical to attempt to control the toner density of a liquid developer so as to be kept at a selected value.

For example, as disclosed in JP 2009-163124 A, a toner density of a liquid developer supplied to a developing machine from a main tank is detected utilizing the fact that the velocity of ultrasonic waves propagating in the liquid developer is varied with the toner density. The toner density of a liquid developer is controlled so that toner densities so detected become identical to a given value (JP 2009-163124 A).

In detecting a toner density as mentioned above, it has also been known that air bubbles if contained in a liquid developer vary the propagation velocity of ultrasonic waves therethrough, leading to a reduction of the detection accuracy of a toner density (see JP 2008-14930 A).

In a toner density detecting apparatus as disclosed in JP 2008-14930 A cited above, only a response time from transmission to reception of one pulse of the ultrasonic waves from an ultrasonic transmitter, in which a propagation velocity per one pulse of the ultrasonic waves is within a selected range of velocities, is used in an attempt to improve the detection accuracy of the toner density if air bubbles are contained in the liquid developer.

In recent years, a deaerator for separating and thereby removing air dissolved in a liquid has been proposed in which a hollow fiber membrane (gas permeable membrane) is utilized.

The hollow fiber membrane has a fiber wall in the form of a straw which is formed with ultrafine holes and in nature is permeated only with dissolved gas of the molecular level existing in a liquid, the fiber wall thereby separating dissolved air and removing the same from the liquid.

For example, as the deaerator for removing a gas (air) dissolved in an ink in an ink jet recording machine there has been proposed one in which numbers of hollow fiber membranes as mentioned above are disposed in a case and passed by the ink through their insides while the inside of the case is depressurized, thereby removing the gas (air) from the ink passing through the inside of the hollow fiber membranes (see JP 2006-281532 A).

While a toner density detecting apparatus as disclosed in JP 2008-14930 A cited above allows a toner density in a liquid developer, even if it contains air bubbles, to be detected with a high degree of precision, to the extent that air bubbles are contained in the liquid developer there exists the possibility that a liquid developer circulating system for detecting the toner density and the printing quality of prints are thereby adversely affected in any way; hence potentially rising the need to further take measures to meet such possibilities.

Also, demanded with a desired increase in printing speed of an electrophotographic printer, an increase in amount of consumption of toner per unit time and an increase in rate of supply of a liquid developer onto a developing machine tend to further grow adverse influences of the existence of air bubbles on the printing quality of prints Whereupon, utilizing a deaerator as disclosed in JP 2006-281532 A which uses a hollow fiber membrane for removing gases in an ink in an ink jet recording machine, the present inventors attempted to remove air dissolved in a liquid developer and causing air bubbles in the liquid developer, but without satisfactory results. In an attempt to detect a toner density of the liquid developer using ultrasonic waves, toner densities could not be detected accurately due to such air bubbles.

Causes of this have been found to be as follows:

A first cause: Having a viscosity higher than that of an ink for an ink jet recording machine, a liquid developer for use in a wet-type electrophotographic printer needs to be passed through the inside (inner diameter portion) of a hollow fiber membrane constituting an aforesaid deaerator and having a diameter of several millimeter, under an elevated pressure to allow the high viscosity liquid developer to flow therethrough at a desired rate of flow. However, for fear the liquid developer under elevated pressure may cause the fiber forming the hollow fiber membrane to peel off, the liquid developer cannot be passed to flow at the desired rate of flow.

A second cause: The rate of flow of the liquid developer of high viscosity when passing to flow through the inside of the hollow fiber membrane is high as desired only in a central region of the inside, but is lowered in its outer region adjacent to the inner peripheral surface (inner wall surface) of the hollow fiber membrane. As a result, air dissolved in the liquid developer becomes hard to flow out through the wall of the hollow fiber membrane, and the efficiency of removal of the dissolved air may become extremely deteriorated.

Made to solve problems as mentioned above, the present invention has for its object to provide an apparatus for detecting a toner density of a liquid developer for an electrophotographic printer whereby in detecting a toner density utilizing the fact that the propagation velocity of ultrasonic waves propagating through the liquid developer changes with a change in toner density, it is made possible to detect a toner density of the liquid developer with a high degree of precision.

DISCLOSURE OF THE INVENTION

There is provided in accordance with the present invention an apparatus for detecting a toner density of a liquid developer, which comprises a liquid developer circulating path for circulating therethrough the liquid developer for an electrophotographic printer stored in a main tank, a deaerator provided in the liquid developer circulating path and a density detector provided downstream of the deaerator in the liquid developer circulating path, wherein the said deaerator has one bundle or a plurality of bundles of hollow fibers, each of the hollow fibers forming a hollow fiber membrane whose inside is adapted to be depressurized and over whose outer peripheral surface the liquid developer is adapted to flow under pressure whereby air dissolved in the liquid developer is forced to permeate the hollow fiber membrane into the inside, and the density detector comprises a flow passage in which the liquid developer is adapted to flow from below upwards, and an ultrasonic transmitter and an ultrasonic receiver which are opposed to each other across said flow passage for transmitting and receiving ultrasonic waves into and from the flow passage, the density detector detecting the toner density of the liquid developer flowing in the flow passage utilizing the fact that propagation velocity of ultrasonic waves that propagate through the liquid developer changes with a change in toner density of the liquid developer.

In the apparatus for detecting a toner density of a liquid developer of the present invention as mentioned above, the deaerator may include: a main body comprising a liquid developer flow chamber and a first and a second vacuum chamber which are disposed at one and the other sides of the liquid developer flow chamber, respectively; and a vacuum pump for depressurizing the first and second vacuum chambers, the one or plurality of bundles of hollow fibers being mounted in the liquid developer flow chamber of the deaerator so that one and the other longitudinal ends of the inside of the hollow fiber membrane formed by each of the said hollow fibers are open to and communicates with said first and second vacuum chambers, respectively.

With the apparatus so configured, the inside of the hollow fiber membrane is depressurized from its both longitudinal ends while the liquid developer is forced to flow over its peripheral surface surely in contact with the peripheral surface of the hollow fiber membrane in the liquid developer flow chamber, making it possible to sufficiently remove dissolved air in the liquid developer at an improved efficiency of deaeration.

In the apparatus for detecting a toner density of a liquid developer of the present invention as mentioned above, the liquid developer flow chamber of the main body of the deaerator has a first and a second region which are positioned closer to one and the other longitudinal ends of the bundle or bundles of hollow fibers, respectively, such that the liquid developer is forced to flow under pressure into and out of the liquid developer flow chamber through the first and second regions, respectively.

With the apparatus configured so, the liquid developer is forced to flow over the peripheral surfaces of the hollow fiber membranes of the hollow fiber bundle in their longitudinal directions. Since the area of contact of the liquid developer with the hollow fiber membranes is thus enlarged, it is made possible for dissolved air in the liquid developer to be removed more sufficiently at a further increased efficiency of deaeration.

According to the present invention, air dissolved in a liquid developer can be sufficiently removed through the deaerator. Subsequently, a toner density is detected utilizing the fact that propagation velocity of ultrasonic waves propagating through a liquid developer changes with a change in toner density of the liquid developer. In detecting the toner density in an area density of detection, the liquid developer is passed to flow from below upwards through the area of density detection, making it hard for air bubbles caused by residual dissolved air to stay in the area of density detection. Only a diminished or minimized amount of air bubbles is present in a flow of the liquid developer whose toner density is detected. Hence, toner densities can be detected with a high degree of precision.

Further, since a liquid developer with which the developing machine is supplied contains only a diminished amount of residual air, prints excellent in printing quality can be obtained.

Yet further, since the apparatus including the deaerator may be given the ability for an increased amount of liquid developer to be passed therethrough, the liquid developer in the main tank can be circulated at an increased rate of flow while its toner density is being detected with a high degree of precision. Thus, in a high-speed printing with an electrophotographic printer as well, it is made possible for the toner density of a liquid developer to be maintained precisely at a selected density.

BEST MODES FOR CARRYING OUT THE INVENTION

Figure 1:
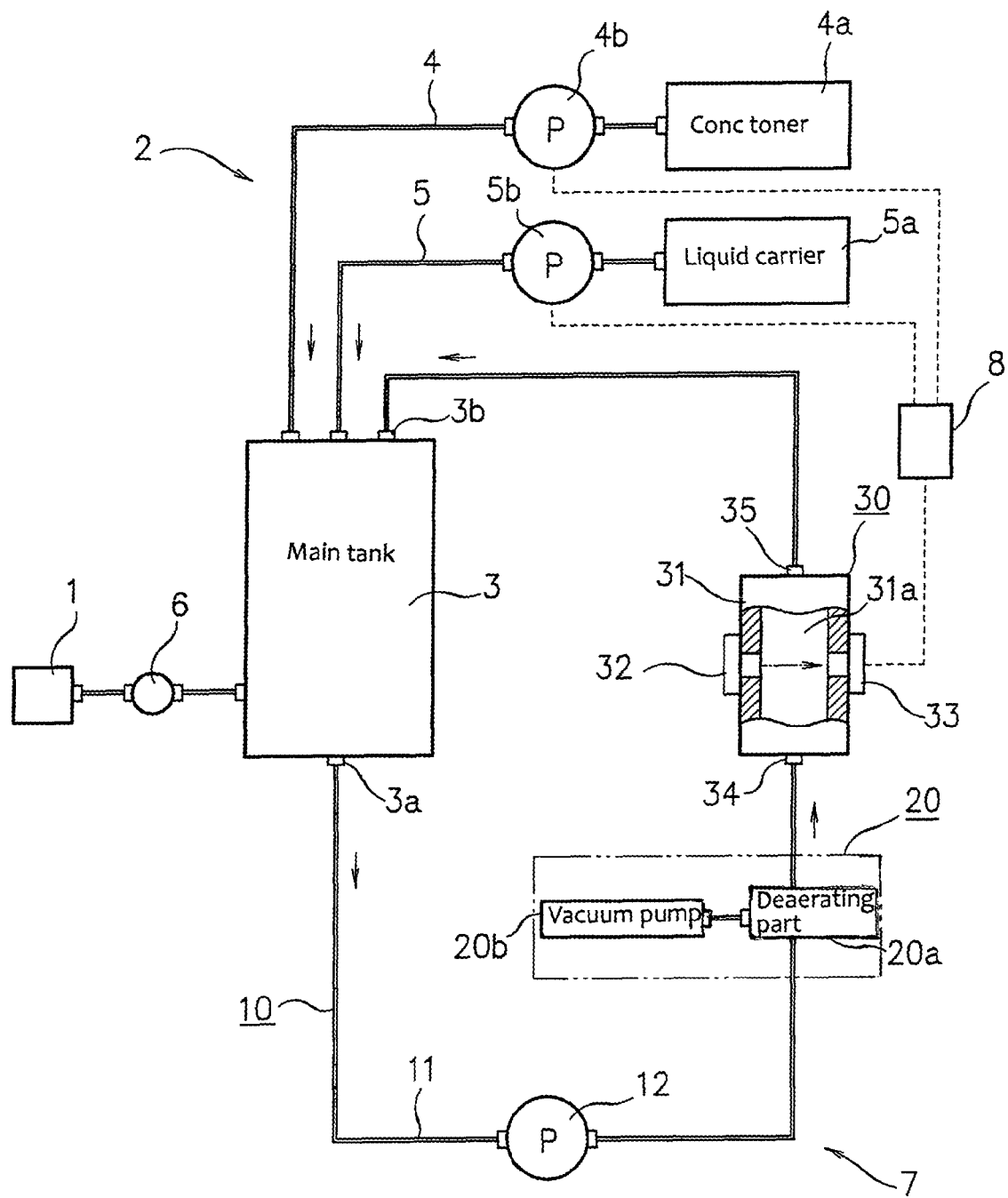
FIG. 1 is a structural explanatory view of a part for supplying a developing machine with a liquid developer, including a liquid developer toner density detecting apparatus as a form of implementation of the present invention.

As shown in FIG. 1, a developing machine (developing roll) 1 in a wet electrophotographic printer is supplied with a liquid developer by a controlled developer supply 2 which includes a main tank 3 for reserving the liquid developer for the electrophotographic printer, a conc toner supply unit 4 for supplying the main tank 3 with a conc toner (concentrated liquid toner), a liquid carrier supply unit 5 for supplying the main tank 3 with a liquid carrier (diluent liquid), and a liquid developer feed pump 6 whereby the developing machine 1 is fed with the liquid developer in the main tank 3.

The conc toner supply unit 4 has a conc toner tank 4a and a conc toner feed pump 4b for feeding the conc toner from the conc toner tank 4a into the main tank 3.

The liquid carrier supply unit 5 has a liquid carrier tank 5a and a liquid carrier feed pump 5b for feeding the liquid carrier from the liquid carrier tank 5a into the main tank 3.

A toner density of the liquid developer in the main tank 3 is detected by a toner density detecting apparatus 7, and a toner density thus detected is transmitted to a toner density control unit 8. By this toner density control unit 8, operations of the conc toner supply unit 4 and carrier liquid supply unit 5 mentioned above are controlled so as to maintain the toner density of the liquid developer in the main tank 3 at a selected value.

For example, when the toner density detected is lower than the selected value, a motor for the conc toner feed pump 4b is driven (overdriven) to feed the conc toner (increase its rate of feed) into the main tank 3 and thereby to raise the toner density in the liquid developer. And, when the toner density detected becomes identical to the selected value, the motor for the conc toner feed pump 4b is ceased whereby the toner density in the liquid developer in the main tank 3 is maintained at the selected value.

When the toner density detected is higher than the selected value, a motor for the carrier feed pump 5b is driven (overdriven) to feed the liquid carrier (increase its rate of feed) into the main tank 3 and thereby to lower the toner density in the liquid developer. And, when the toner density detected becomes identical to the selected value, the motor for the carrier feed pump 5b is ceased whereby the toner density in the liquid developer in the main tank 3 is maintained at the selected value.

As mentioned above the conc toner supply unit 4, the liquid carrier supply unit 5, the toner density detection unit 7 and the toner density control unit 8 make up a toner density control system.

The toner density detecting unit 7 mentioned above includes a liquid developer circulating path 10 through which the liquid developer stored in the main tank 3 is circulated, a deaerator 20 provided in the liquid developer circulating path 10, and a density detector 30, a toner density detected by which is transmitted to the toner density control unit 8.

The liquid developer circulating path 10 mentioned above is provided with a communication pipeline 11 which communicates between an outlet 3a and a return port 3b of the main tank 3 and communicates with a circulating pump 12 by which the liquid developer is driven to flow through the communication pipeline 11 for feeding out the liquid developer in the main tank 3 through the outlet 3a and returning it into the main tank 3 through the return port 3b.

Figure 2:
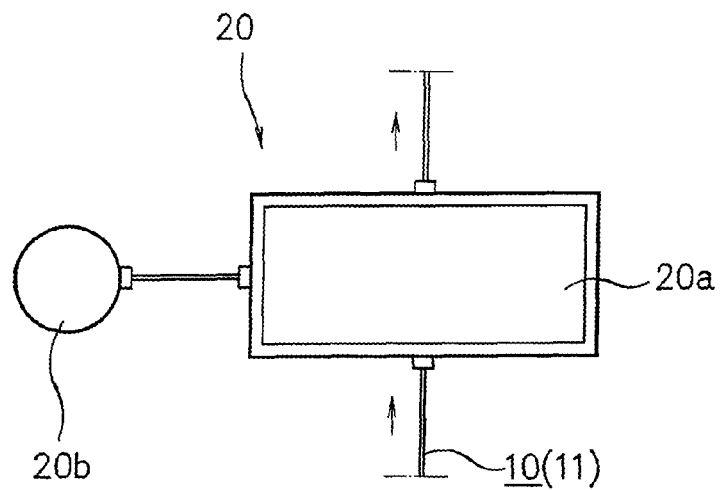
FIG. 2 is a schematic explanatory view of a deaerator in the form of implementation.

The deaerator 20 mentioned above is provided, as shown in FIG. 2, with a deaerating part 20a through which is passed to flow the liquid developer circulating along the liquid developer circulating path 10 and with a vacuum pump 20b for depressurizing the inside of the deaerating part 20a.

Figure 3:
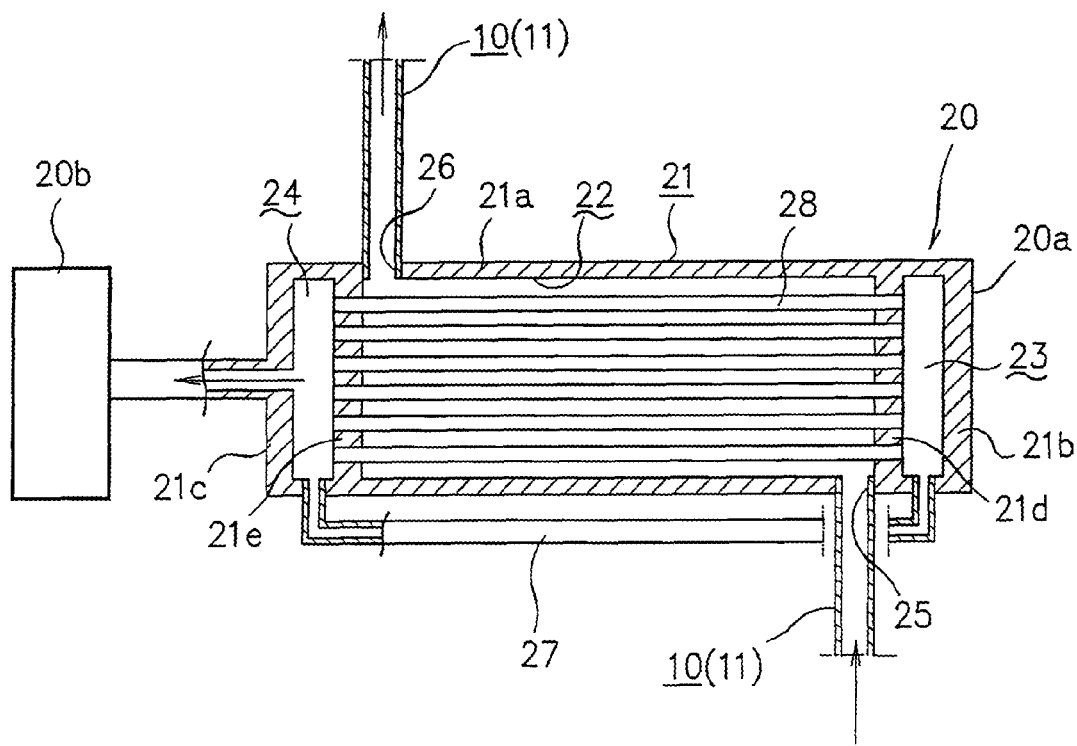
FIG. 3 is a detailed view, in part cut away, of the deaerator.

The deaerating part 20a as shown in FIG. 3 has a main body 21.

The main body 21 has an outer peripheral wall 21a, a first end wall 21b occluding an opening at one end of the outer peripheral wall 21a, a second end wall 21c occluding an opening at the other end of the outer peripheral wall 21a, a first partition wall 21d close to the one end of the outer peripheral wall 21a and, a second partition wall 21e close to the other end, which form a liquid developer flow chamber 22, a first vacuum chamber 23 positioned at one side of the liquid developer flow chamber 22 and a second vacuum chamber 24 positioned at the other side of the liquid developer flow chamber 22.

The outer peripheral wall 21a is formed with an inlet port 25 and an outlet port 26 such that they open to the liquid developer flow chamber 22, the first and second vacuum chambers 23 and 24 communicating with each other via a vacuum chamber communicating path 27.

The vacuum pump 20b has its suction or intake port communicating with the second vacuum chamber 24 to draw in air in the second vacuum chamber 24 by suction.

The liquid developer flow chamber 22 mentioned above is provided with a plurality of bundles 28 of hollow fibers arranged so that the bundles 28 are spaced apart from one another so as to form a spacing between adjacent bundles 28. Each such bundle 28 of hollow fibers is supported by the first partition wall 21d and the second partition wall 21e, and has one and the end faces open to and communicating with the first and second vacuum chambers 23 and 24, respectively.

Figure 4:
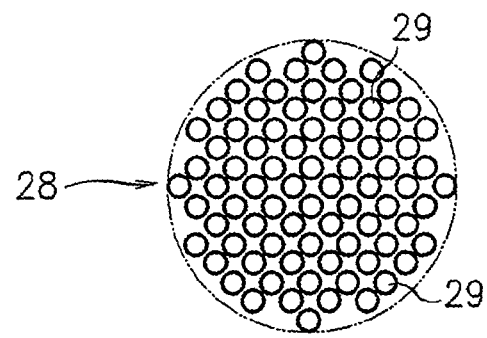
FIG. 4 is an enlarged cross-sectional view of a bundle of hollow fibers in the deaerator.

Each of the bundles 28 of hollow fibers mentioned above is a bundle of many hollow fiber membranes 29 as shown in FIG. 4.

Figure 5:
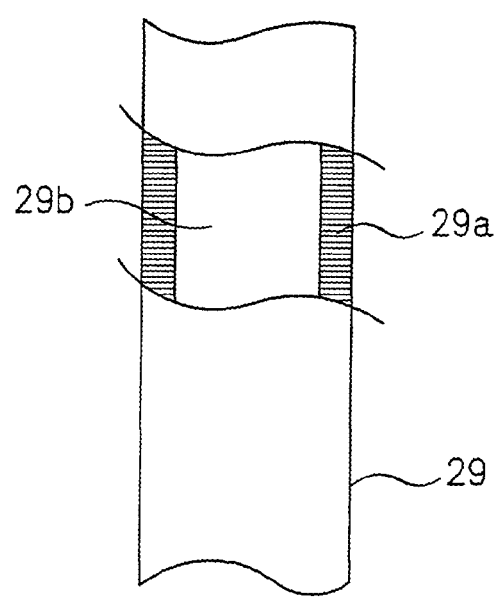
FIG. 5 is an explanatory view of a hollow fiber membrane in the bundle of hollow fibers.

Each hollow fiber membrane 29 as shown in FIG. 5 is of a fiber in the form of a pipe having an outer diameter of 0.3 to 0.4 mm, whose inside 29b is hollow and whose peripheral wall 29a is formed therethrough with a very large number of ultrafine holes impermeable with a liquid and permeable only with air or a gas.

To wit, the deaerator 20 is so made up that the inside 29b of each hollow fiber membrane 29 of one bundle or a plurality of bundles of hollow fibers 28 communicates with the first and second vacuum chambers 23 and 24 depressurized by the vacuum pump 20b. Each hollow fiber membrane 29 is solidly supported at its both longitudinal end portions by the wall face makeup components (partition walls 21d and 21e) so that its longitudinal intermediate portion is positioned within the hermetically sealed space (in the liquid developer flow chamber 22). And, a hollow fiber bundle 28 is peripherally surrounded with the outer wall (outer peripheral wall 21a) which has the inlet and outlet ports 25 and 26 for the liquid developer so that the liquid developer may be passed to flow over and along the outer peripheral surface of the hollow fiber bundle 28.

The inlet and outlet ports 25 and 26 mentioned above communicate with the communication pipeline 11 at its upstream and downstream sides, respectively. With the circulating pump 12 driven, the liquid developer from the main tank 3 is passed to flow through the liquid developer flow chamber 22 in which air dissolved in the liquid developer is fully separated and removed therefrom through the hollow fiber bundle 28 (a hollow fiber membrane 29).

To wit, here the liquid developer flowing over and along the outer peripheral surface of a hollow fiber bundle 28 (a hollow fiber membrane 29), i.e., the hollow fiber bundle 28 (hollow fiber membrane 29) receiving pressure of the liquid developer externally applied prevents the hollow fiber bundle 28 (hollow fiber membrane 29) from peeling off even if the liquid developer is a liquid developer of high viscosity and flowing under an elevated pressure. Hence, without fear of such breaking- or peeling-off, the liquid developer is allowed to flow at an increased rate of flow and thus at a desired rate of flow.

This allows a liquid developer to flow (circulate) along the liquid developer circulating path 10 at a necessitated, increased rate of flow (circulation).

Moreover, the liquid developer flows over and while certainly in contact with the outer peripheral surface (outer diametrical area) of the hollow fiber bundle 28 (hollow fiber membrane 29) and having an increased area of their contact compared with the case of flowing through its inside. This facilitates it for air dissolved in the liquid developer to permeate the wall (peripheral wall 29a) of the hollow fiber bundle 28 (hollow fiber membrane 29) into the inside 29b of the fiber membrane 29, and increases the efficiency of removal of air dissolved.

In this form of implementation of the present invention, the inlet and outlet ports 25 and 26 mentioned above are positioned to lie close to the first and second partition walls 21d and 21e, respectively, so that the liquid developer flowing from the inlet port 25 into the liquid developer flow chamber 22 is passed to flow longitudinally of and over the hollow fiber bundles 28 and flows out of the outlet port 26 with the result of a further increased area of flow contact of the liquid developer with each of the hollow fiber bundles 28 and hence an further improved efficiency of removal of dissolved air.

These in combination allow air dissolved in the liquid developer to be sufficiently removed, enhancing the effectiveness of deaeration.

According to the deaerator 20 mentioned above, therefore, an increase in the rate of removal of dissolved air per unit rate of flow, coupled with the possibility to remove air dissolved in a liquid developer larger in amount than that possible with the conventional deaerator while the liquid developer is being circulated through the liquid developer circulating path 10, makes it possible to lower the proportion of residual dissolved air in the liquid developer. Residual dissolved air in the liquid developer forwarded to the developing machine 1 can thus be reduced, enhancing the printing quality of prints.

Yet further, the aforementioned deaerator 20 possible to remove air dissolved in a larger amount of the liquid developer can amply meet with the demands for an increase in amount of consumption of the liquid developer and an increase in capacity of the main tank 3 reserving the liquid developer, which are needed to meet with an increase as desired in printing speed of an electrophotographic printer.

Also, the deaerator 20 can be modified to meet with various specifications such as in processing capacity and deaerating capability as required therefor, by settings of the arrangement of the hollow fiber bundles 28 in the liquid developer flow chamber 22 of the main body 21 of the deaerator 20 and the rate of flow of the liquid developer therein. It is thus possible to plan to provide a deaerator and a toner density detector that meet with a wide range of requirement specifications.

In the form of implementation illustrated, air is drawn by suction from the longitudinal end portions of a or each hollow fiber bundle 28 (hollow fiber membrane 29) to depressurize (to make negative pressure in) its inside 29b. By reducing pressure in the inside 29b, air dissolved in the liquid developer is made still easier to flow in and can be removed still more sufficiently. A further enhancement in the effect of deaeration is thereby attained.

The density detector 30 mentioned above includes a detector main body 31 having a flow passage 31a through which the liquid developer removed of dissolved air by the aforementioned deaerator 20 is passed to flow, and an ultrasonic transmitter 32 and an ultrasonic receiver 33 which are opposed to each other across the flow passage 31a.

And, with the ultrasonic receiver 33 receiving ultrasonic waves transmitted from the ultrasonic transmitter 32 into the liquid developer flowing through its flow passage, a propagation velocity of the ultrasonic waves propagating through the liquid developer is detected to detect a toner density of the liquid developer in proportion to the detected ultrasonic propagation velocity.

Since as mentioned above, air dissolved in the liquid developer flowing through the flow passage of the detector main body 31 is reduced and air bubbles in the liquid developer flowing through the flow passage is diminished, the detection accuracy of a toner density becomes little affected by any residual air bubbles that may be left unremoved, and thus the toner density is detected with a high degree of precision.

The detector main body 31 mentioned above has an inlet 34 at its upper side and an outlet 35 at its lower side.

And, the inlet 34 communicates with an upstream side of the aforementioned communication pipeline 11, the upstream side communicating with the deaerator 20, and outlet 35 communicates with a downstream side of the communication pipeline 11, the downstream side communicating with the main tank 3. The flow passage 31a is so oriented in the detector main body 31 that the liquid developer flows therethrough from below upwards.

The ultrasonic transmitter 32 and the ultrasonic receiver 33 are so arranged that ultrasonic waves are transmitted and received in a direction perpendicular to the direction in which the liquid developer is passed to flow in the flow passage 31a.

With such arrangements as mentioned above, dissolved air in the liquid developer flowing from below upwards in the flow passage 31a of the detector main body 31 is restrained from adhering on a wall surface of the flow passage 31a and on a surface of the ultrasonic detecting face and becoming such air bubbles which affect the detection of propagation velocity of ultrasonic waves.

In specific terms, buoyancy of such air bubbles and upward flow of the liquid developer make it impossible for such any air bubble to adhere and to grow on a surface of the flow passage 31a and on a surface of the ultrasonic detecting face. Such air bubbles are made impossible to stay in the flow passage.

It follows, therefore, that if air dissolved in the liquid developer is left not completely removed by the deaerator 20, a toner density of the liquid developer can yet be detected with a high degree of precision by the density detector 30, and the error in toner density is diminished between a toner density of the liquid developer in the main tank 3 and a toner density of the liquid developer flowing in the flow passage 31a of the toner density detector 30, making it possible to detect a toner density of the liquid developer in the main tank 3 with a high degree of precision.

To wit, by providing the liquid developer circulating path 10 to pass the liquid developer from the main tank 3 to normally circulate and flow through the deaerator 20 and the density detector 30 where the deaerator 20 is so configured as to enable dissolved air in the circulating liquid developer to be removed efficiently and further the density detector 30 is so configured as to make an air bubble hard to stay in an area of density detection (an area through which ultrasonic waves propagate), there are provided toner density detecting conditions whereby the toner detection is not the least affected by such air bubbles due to a maximum limit in amount of dissolved air. Hence, a toner density of the liquid developer can be detected with a high degree of precision.

And, based on a toner density thus detected at high precision, the toner density is controlled by the toner density control unit 8 which is provided to control supply of a conc toner and a carrier liquid. With toner densities of the liquid developer thus maintained stably at a selected value, prints can be yielded that are excellent and stabilized in printing quality.

What is claimed is:

1. An apparatus for detecting a toner density of a liquid developer, comprising:
    a liquid developer circulating path for circulating therethrough the liquid developer for an electrophotographic printer stored in a main tank,
    a liquid developer feeding path for feeding the liquid developer stored in the main tank to a developing machine provided outside the liquid developer circulating path,
    a deaerator provided in the liquid developer circulating path and
    a density detector provided downstream of the deaerator in the liquid developer circulating path,
    wherein said deaerator has one bundle or a plurality of bundles of hollow fibers, each of the hollow fibers being formed of a bundle of hollow fiber membranes,
    wherein the inside of the hollow fiber membrane is depressurized and the liquid developer is configured to flow under pressure over the outer peripheral surface of the hollow fiber membrane, whereby air dissolved in the liquid developer is forced to permeate the hollow fiber membrane into said inside of the hollow fiber membrane, and
    said density detector comprises
        a flow passage, wherein the liquid developer flows from below upwards; and
        an ultrasonic transmitter and an ultrasonic receiver, which are opposed to each other across said flow passage, for transmitting and receiving ultrasonic waves into and from the fluid passage,
    the density detector detects the toner density of the liquid developer flowing in the flow passage due to the propagation velocity of ultrasonic waves that propagate through the liquid developer changing with a change in toner density of the liquid developer.

2. The apparatus for detecting a toner density of a liquid developer as set forth in claim 1, wherein
    said deaerator comprises:
    a main body comprising a liquid developer flow chamber and a first vacuum chamber and a second vacuum chamber, wherein said first vacuum chamber and said second vacuum chamber are disposed at one side and the opposing side of the liquid developer flow chamber, respectively; and a vacuum pump for depressurizing said first vacuum chamber and second vacuum chamber, wherein said one or plurality of bundles of hollow fibers are mounted in the liquid developer flow chamber so that both longitudinal ends of the inside of the hollow fiber membrane are open to and communicates with said first vacuum chamber and said second vacuum chamber, respectively.

3. The apparatus for detecting a toner density of a liquid developer as set forth in claim 2, wherein the liquid developer flow chamber has a first region and a second region, which are positioned close to one and the other longitudinal ends of said bundle or bundles of hollow fibers, respectively, such that the liquid developer is forced to flow under pressure into and out of said liquid developer flow chamber through said first region and said second region, respectively.

4. The apparatus for detecting a toner density of a liquid developer as set forth in claim 1, wherein the hollow fiber membrane is a fiber in the form of a pipe having an outer diameter of 0.3 to 0.4 mm.

5. The apparatus for detecting a toner density of a liquid developer as set forth in claim 1, wherein the inside of the hollow fiber membrane is hollow and wherein the outer peripheral surface of the hollow fiber membrane is formed with a plurality of ultrafine holes that are permeable only to air or a gas.

6. The apparatus for detecting a toner density of a liquid developer as set forth in claim 1, wherein when the toner density of the liquid developer is lower than a preselected value detected by said density detector, a concentrated supply of toner is feed into the liquid developer circulating path by a conc toner feed pump.

7. The apparatus for detecting a toner density of a liquid developer as set forth in claim 1, wherein when the toner density of the liquid developer is higher than a preselected value detected by said density detector, a diluent liquid is feed into the liquid developer circulating path by a carrier feed pump.

* * * * *